United States Patent
Cross et al.

(10) Patent No.: US 7,050,176 B1
(45) Date of Patent: May 23, 2006

(54) SENSOR ASSEMBLY

(75) Inventors: Graham Cross, Stockton-on-Tees (GB);
Neville John Freeman, Tarporley (GB);
Marcus Swann, Durham (GB)

(73) Assignee: Farfield Sensors Limited, Manchester (GB)

( * ) Notice: Subject to any disclaimer, the term of this patent is extended or adjusted under 35 U.S.C. 154(b) by 387 days.

(21) Appl. No.: 10/204,853

(22) PCT Filed: Nov. 10, 2000

(86) PCT No.: PCT/GB00/04298

§ 371 (c)(1),
(2), (4) Date: Oct. 22, 2002

(87) PCT Pub. No.: WO01/36946

PCT Pub. Date: May 25, 2001

(30) Foreign Application Priority Data

Nov. 18, 1999 (GB) .................................. 9927248

(51) Int. Cl.
*G01B 9/02* (2006.01)
(52) U.S. Cl. .................................................. 356/517
(58) Field of Classification Search ................. 356/477, 356/484, 491, 517; 385/12
See application file for complete search history.

(56) References Cited

U.S. PATENT DOCUMENTS

| | | | | |
|---|---|---|---|---|
| 5,082,629 A | * | 1/1992 | Burgess et al. | 422/82.11 |
| 5,132,097 A | * | 7/1992 | Van Deusen et al. | 422/82.09 |
| 5,455,178 A | | 10/1995 | Fattinger | 436/164 |

FOREIGN PATENT DOCUMENTS

| | | |
|---|---|---|
| EP | 0 478 137 A2 | 8/1991 |
| EP | 0 478 137 A3 | 8/1991 |
| WO | WO 91/02239 | 2/1991 |

OTHER PUBLICATIONS

Integrated optical chemical and direct biochemical sensors by W. Lukosz; printed 1995; pp. 37-50.
Electronics Letters; Waveguide Zeeman interferometry for thin-film chemical sensors by K.M. Grace et al.; vol. 33, No. 19; printed Sep. 11, 1997; pp. 1651-1653.

* cited by examiner

*Primary Examiner*—Hwa (Andrew) Lee
*Assistant Examiner*—Michael A. Lyons
(74) *Attorney, Agent, or Firm*—Stoel Rives LLP (57) ABSTRACT

The present invention relates to a sensor assembly and method for measuring changes in dimension and/or composition of a sensor component (and associated factors) caused by the introduction of or changes in a chemical, physical or biological stimulus in a localized environment.

41 Claims, 2 Drawing Sheets

SENSOR ASSEMBLY

RELATED APPLICATIONS

This utility application claims priority to PCT Application Serial No. PCT/GB00/04298, filed on Nov. 10, 2000 entitled SENSOR ASSEMBLY.

TECHNICAL FIELD

The present invention relates to a sensor assembly and method for measuring one or more factors contributing to a change in the effective refractive index of a sensor component caused by the introduction of or changes in a stimulus in a localised environment (e.g. changes in dimension and/or composition of a sensor component caused by the introduction of or changes in a chemical, physical or biological stimulus in a localised environment).

BACKGROUND OF THE INVENTION

In conventional optical waveguide sensor assemblies, it is difficult to determine the precise nature of any change in the effective refractive index of the sensor component i.e. the factors such as changes in dimension (e.g. physical thickness) and/or changes in composition (i.e. intrinsic refractive index) which contribute to changes in effective refractive index cannot be differentiated. This may be problematic for a number of reasons. For example, as a consequence of vapour ingress into an absorption layer, the contribution of changes in intrinsic refractive index may be opposite to the contribution of changes in refractive index due to physical swelling. This not only reduces the effectiveness of the sensor component but also ensures that the aggregate response is a non-linear function of the vapour concentration.

Generally speaking, it is known to make use of the evanescent field component of electromagnetic radiation incident on a waveguide structure (i.e. the field which extends outside the guiding region) to sense discrete changes in optical properties (see inter alia GB-A-2228082, U.S. Pat. No. 5,262,842, WO-A-97/12225 and GB-A-2307741). This technique relies on "leakage" of optical signals from a waveguide into a sensing layer typically formed from an absorbent polymer. The evanescent component of the optical signal being guided by the waveguide is typically small leading to limited interrogation of the sensing layer. Surface plasmon resonance techniques are also well known to those skilled in the art. Both of these techniques are frequently used in a "difference" mode i.e. where TE (transverse electric) and TM (transverse magnetic) modes are excited simultaneously to determine changes in effective refractive index. In the case of surface plasmon resonance techniques, it is the interaction solely of the TM mode with the analyte that is detected. In neither case has the interaction of both the TE and TM modes been exploited to differentiate factors contributing to changes in effective refractive index.

Additional aspects and advantages of this invention will be apparent from the following detailed description of preferred embodiments thereof, which proceeds with reference to the accompanying drawings.

BRIEF DESCRIPTION OF THE DRAWINGS

The present invention will now be described in a non-limitative sense with reference to the accompanying Figures in which.

DETAILED DESCRIPTION OF PREFERRED EMBODIMENTS

Based on the principle of interferometry (which is itself a well-established technique), the present invention provides a novel sensor assembly which may be interrogated in a novel manner such that the factors (e.g. dimensional and compositional) contributing to changes in the effective refractive index of the sensor assembly may be differentiated. The sensor assembly is robust whilst providing high performance in terms of sensitivity and selectivity which optimises the field of use.

Thus viewed from one aspect the present invention provides a sensor assembly for measuring one or more factors contributing to a change in the effective refractive index of a sensor component thereof caused by the introduction of or changes in a stimulus (e.g. a chemical, physical or biological stimulus) in a localised environment, wherein said sensor component includes: either (1) one or more sensing layers capable of inducing a measurable response to a change in the localised environment caused by the introduction of or changes in the stimulus, or (2) a sensing waveguide capable of exhibiting a measurable response to a change in the localised environment caused by the introduction of or changes in the stimulus, said sensor assembly further comprising: first irradiating means for irradiating the sensor component with electromagnetic radiation in TM mode; and second irradiating means for irradiating the sensor component with electromagnetic radiation in TE mode.

Viewed from a further aspect the present invention provides a method for measuring one or more factors contributing to a change in the effective refractive index of a sensor component caused by the introduction of or changes in a stimulus (e.g. a chemical, physical or biological stimulus) in a localised environment, said method comprising: (A) providing a sensor assembly as hereinbefore defined; (B) introducing the stimulus into the localised environment; (C) irradiating the sensor component with electromagnetic radiation in TE mode to produce a first interference pattern; (D) irradiating the sensor component with electromagnetic radiation in TM mode to produce a second interference pattern; (E) measuring movements in the first interference pattern; (F) measuring movements in the second interference pattern; and (G) relating the movements in the first and second interference patterns to the one or more factors contributing to a change in the effective refractive index of the sensor component.

In accordance with the invention, electromagnetic radiation in TE and TM modes may be used to measure an optical response (such as movement of fringes) which may be related to factors contributing to changes in the effective refractive index of the sensing layer or sensing waveguide e.g. changes in dimension (e.g. thickness) and/or composition (i.e. intrinsic refractive index) of the sensing layer or sensing waveguide. By allowing the user to differentiate between the dimensional and compositional changes which give rise to the optical response, the utility of this type of sensor assembly is enhanced.

Preferably the one or more factors are changes in dimension (e.g. thickness) and/or composition (i.e. intrinsic refractive index) of either the one or more sensing layers or the sensing waveguide.

Biosensor systems can be expected to exhibit both desired specific binding interactions alongside unwanted non-specific binding interactions which limits their effective integration onto optical sensor components. By way of example (but not wishing to be bound by theory), where an antibody is bound to the surface of the sensor component within either a sensing waveguide or a sensing layer, specific binding of an antigen gives rise to a dimensional change which dominates the compositional change. On the other hand, non-specific binding gives rise to a compositional change which dominates the dimensional change. Thus in a preferred embodiment of the sensor assembly or method of the invention the one or more factors contributing to a change in the effective refractive index of a sensor component are specific and/or non-specific binding. By allowing these effects to be distinguished, this embodiment of the present invention permits integration into biochemical systems.

In a preferred embodiment of the sensor assembly and method of the invention, the one or more factors contributing to a change in the effective refractive index of a sensor component are a conformational change of the stimulus. For example, the stimulus may be a protein which undergoes a conformational change by a change in temperature, pH or by interaction with an additional species. By way of example (but not wishing to be bound by theory), hexakinase on the surface of the sensor component within either a sensing waveguide or a sensing layer undergoes a conformational change in the presence of glucose giving rise to a dimensional change which dominates the compositional change. The present invention makes it possible to distinguish this dimensional change from the compositional change so as to deduce the conformational change.

In a preferred embodiment of the sensor assembly and method of the invention, the one or more factors contributing to a change in the effective refractive index of a sensor component are nucleotide complementation. By way of example (but not wishing to be bound by theory), a nucleotide strand on the surface of the sensor component within either a sensing waveguide or a sensing layer gives rise to a dimensional change which dominates the compositional change when it undergoes effective nucleotide complementation (a technique commonly referred to as SNIP). The present invention makes it possible to distinguish this dimensional change from the compositional change so as to identify effective nucleotide complementation.

Preferably the one or more factors contributing to a change in the effective refractive index of the sensor component are ingress of a chemical stimulus into or depletion of a chemical stimulus from the sensing layer or the sensing waveguide.

Preferably the one or more factors contributing to a change in the effective refractive index of the sensor component are expansion or contraction of the sensing layer or sensing waveguide (e.g. in the form of a thin film). The present invention makes it possible to distinguish the dimensional change from the compositional change thereby providing a new use for a sensor assembly of this type.

Preferably the one or more factors contributing to a change in the effective refractive index of the sensor component are the characteristics of adsorption of large non-spherical biological molecules from an aqueous solution. The present invention makes it possible to distinguish dimensional change from compositional change. In this embodiment, changes in the film thickness would be indicative of the molecular orientation and changes in the intrinsic refractive index indicative of the density of adsorption.

Preferably the method of the invention further comprises: calculating the phase shift from the movements in the first and second interference patterns and relating the phase shift to the one or more factors contributing to a change in the effective refractive index of the sensor component.

The first and second irradiating means may be adapted to irradiate the sensor component with electromagnetic radiation in TE or TM mode sequentially or simultaneously.

The first and second irradiating means may comprise the same or different electromagnetic radiation sources. Where different sources are used, an optical switch (e.g. a rotating mirror) may be used to switch rapidly between the two. Alternatively, a single electromagnetic radiation source may be used to simultaneously excite TE and TM modes of the sensor component by aligning the polarisation vector of the linearly polarised optical source at an angle of 45< with respect to the plane of the sensing waveguide or sensing layer of the sensor component. An active analyser system may be used to alternately remove the unwanted TE or TM mode radiation during data capture of the desired TM or TE output radiation respectively. The active analyser system may comprise an electro-optic half wave plate placed in series with an analyser.

In a preferred embodiment, an adjustable analyser may be used to measure first and second interference patterns separately. The measurements may be synchronised with the excitation and/or polarisation procedure to ensure that phase shift information is correlated with TE and TM excitation.

A controller may be provided to synchronise the one or more electromagnetic radiation sources and one or more detectors. For example, the controller may capture the data from a photodetector (e.g. photodiode) array. The firing of the (or each) electromagnetic radiation source may be synchronised by the controller with the alternate capture of the interference patterns generated in TM mode and TE mode. The controller may be adapted to calculate the phase shift in TE and TM modes independently.

Preferably the sensor component of the sensor assembly of the invention is adapted so as to be usable in evanescent mode or whole waveguide mode.

Thus in a first embodiment of the sensor assembly, the sensor component includes one or more sensing layers capable of inducing in a secondary waveguide a measurable response to a change in the localised environment caused by the introduction of or changes in the stimulus.

In this first embodiment, the sensor assembly is advantageously adapted to optimise the evanescent component so as to induce in the secondary waveguide a measurable optical response. The sensor component may comprise a plurality of separate sensing layers to enable changes at different localised environments to be measured.

In a preferred sensor assembly of the invention, the sensing layer comprises an absorbent material (e.g. a polymeric material such as polymethylmethacrylate, polysiloxane, poly-4-vinylpyridine) or a bioactive material (eg containing antibodies, enzymes, DNA fragments, functional proteins or whole cells). The absorbent material may be capable of absorbing a gas, a liquid or a vapour containing a chemical stimulus. The bioactive material may be appropriate for liquid or gas phase biosensing. For example, the sensing layer may comprise a porous silicon material optionally biofunctionalised with antibodies, enzymes, DNA fragments, functional proteins or whole cells.

In a preferred sensor assembly of the invention, the secondary waveguide comprises silicon oxynitride or silicon nitride.

In a second embodiment of the invention, the sensor component includes a sensing waveguide capable of exhibiting a measurable response to a change in the localised environment caused by the introduction of or changes in the stimulus.

In this second embodiment, the sensor assembly is adapted to minimise the evanescent component and may be used advantageously in a whole waveguide mode.

In a preferred sensor assembly of the invention, the sensing waveguide comprises an absorbent material (eg a polymeric material such as polymethylmethacrylate, polysiloxane, poly-4-vinylpyridine) or a bioactive material (eg containing antibodies, enzymes, DNA fragments, functional proteins or whole cells).

The absorbent material may be capable of absorbing a gas, a liquid or a vapour containing a chemical stimulus. The bioactive material may be appropriate for liquid or gas phase biosensing. For example, the sensing waveguide may comprise a porous silicon material optionally biofunctionalised with antibodies, enzymes, DNA fragments, functional proteins or whole cells.

Where the sensor component of the sensor assembly of the invention comprises a sensing waveguide adapted for use in whole waveguide mode, an absorbent layer in the form of an overcoating may be present for use as a membrane (for example) to separate out certain stimuli.

To optimise the performance of the first embodiment, the sensor component may further comprise an inactive secondary waveguide in which the sensing layer is incapable of inducing a measurable response to a change in the localised environment caused by the introduction of or changes in the stimulus. The inactive secondary waveguide is capable of acting as a reference layer. It is preferred that the secondary waveguide and inactive secondary waveguide have identical properties with the exception of the response to the change in the localised environment caused by the introduction of or changes in the stimulus. By way of example, the secondary waveguide and inactive secondary waveguide is made of silicon oxynitride.

To optimise the performance of the second embodiment, the sensor component may further comprise an inactive (eg deactivated) waveguide substantially incapable of exhibiting a measurable response to a change in the localised environment caused by the introduction of or changes in the stimulus. The inactive waveguide is capable of acting as a reference layer. The physical, biological and chemical properties of the sensing waveguide and inactive waveguide are as similar as possible (with the exception of the response to the change in the localised environment caused by the introduction of or changes in the stimulus). Typically the inactive waveguide is made of silicon oxynitride.

Preferably each of the sensing waveguide or secondary waveguide (or any additional waveguides such as reference waveguides) of the sensor component is a planar waveguide (ie a waveguide which permits light propagation in any arbitrary direction within the plane).

Preferably, the sensor component of the sensor assembly of the invention constitutes a multi-layered structure (eg a laminated waveguide structure). In this sense, the sensor assembly is simple to fabricate and fault tolerant in terms of construction errors. In a preferred embodiment, each of the plurality of layers in the multi-layered sensor component are built onto a substrate (eg of silicon) through known processes such as PECVD, LPCVD, etc. Such processes are highly repeatable and lead to accurate manufacture. Intermediate transparent layers may be added (eg silicon dioxide) if desired. Typically the sensor component is a multilayered structure of thickness in the range 0.2–10 microns. A layered structure advantageously permits layers to be in close proximity (eg a sensing waveguide and an inactive (reference) waveguide may be in close proximity to one another so as to minimise the deleterious effects of temperature and other environmental factors).

Preferably, the sensor component comprises a stack of transparent dielectric layers wherein layers are placed in close proximity. Preferably each layer is fabricated to allow equal amounts of optical radiation to propagate by simultaneous excitation of the guided modes in the structure. Particularly preferably, the amount of radiation in the sensing waveguide/inactive waveguide or in the secondary waveguide/inactive secondary waveguide is equal.

In a preferred embodiment of the sensor assembly of the invention, the sensor component is of the type described in a PCT application filed in the name of Farfield Sensors Limited claiming priority from GB9927249.4 with the title Sensor Device.

Preferably the sensor assembly comprises: means for measuring the response (to the change in the localised environment caused by the introduction of or changes in the stimulus) of the sensor component.

The sensor assembly of the invention may advantageously be used for measuring changes in dimension and/or composition of a sensor component caused by the introduction of or changes in a chemical stimulus (ie a chemical sensor assembly). For example, a gas or liquid comprising chemical stimuli may be introduced into the sensor assembly. The interaction of the chemical stimulus with the sensing waveguide or sensing layer may be a binding interaction or absorbance or any other interaction. Alternatively, a chemical reaction may take place which causes changes in the nature of the chemical stimuli in situ in the localised environment.

The sensor assembly of the invention may be used to measure inter alia pressure, position, temperature or vibration in relation to the introduction of or changes in a physical stimulus (ie a physical sensor assembly). The physical stimulus may be applied to the sensing layer or sensing waveguide of the sensor component via an impeller (for example) located on the sensing layer or sensing waveguide.

Electromagnetic radiation generated from a conventional source may be propagated into the sensor component in a number of ways. In a preferred embodiment, electromagnetic radiation is simply input via an end face of the sensor component (this is sometimes described as "an end firing procedure"). Preferably (but not essentially), the electromagnetic radiation source provides incident electromagnetic radiation having a wavelength falling within the optical range. Propagating means may be employed for substantially simultaneously propagating incident electromagnetic radiation into a plurality of waveguides. For example, one or more coupling gratings or mirrors may be used. A tapered end coupler rather than a coupling grating or mirror may be used to propagate radiation into the lowermost waveguide.

The incident electromagnetic radiation may be oriented (eg plane polarised) as desired using an appropriate polarising means. The incident electromagnetic radiation may be focussed if desired using a lens or similar micro-focussing means.

Electromagnetic radiation may be modulated (amplitude, frequency or phase for example) to provide additional information on the behaviour of the sensor assembly. Using electromagnetic radiation of different frequencies (either simultaneously or sequentially) varies the contributions of the various waveguides and may further enhance the utility of the sensor assembly.

As a consequence of the introduction of or changes in a physical, biological and/or chemical stimulus in the localised environment (ie a change in the refractive index of material in the localised environment), changes in the dielectric properties (eg the effective refractive index) of the sensing waveguide or sensing layer occur (to which the contributory factors are changes in the intrinsic refractive index and/or the thickness of the sensing waveguide or sensing layer). This causes a measurable optical response (ie a change in the transmission of electromagnetic radiation down the sensing waveguide (or waveguides) in whole waveguide mode or the secondary waveguide in evanescent field mode) which in one embodiment manifests itself as a movement of interference fringes which differs according to whether the sensor component is interrogated in TE or TM mode.

By way of example, the movement of the first or second interference pattern may be used to calculate the phase shift which takes place in the sensing waveguide or sensing layer during the passage of electromagnetic radiation through the sensor component. The phase shift is effectively directly proportional to changes occurring in the effective refractive index of the sensing waveguide or sensing layer and differs according to whether the sensor component is interrogated in TE or TM mode.

First and second interference patterns for TE and TM modes respectively may be generated when the electromagnetic radiation from the sensor component is coupled into free space and may be recorded in a conventional manner (see for example WO-A-98/22807). An optical response of the sensor component to a change in the localised environment may be measured from movement of the fringes in the first and the second interference pattern. The phase shift of the radiation in the sensor component (eg induced in the secondary waveguide in evanescent field mode or exhibited in the sensing waveguide in whole waveguide mode) may be calculated. In turn, a measurement of the one or more factors contributing to a change in the effective refractive index may be calculated (eg changes in dimension and/or composition of the sensing waveguide or sensing layer may be calculated).

Movement in the interference fringes may be measured either using a single detector which measures changes in the electromagnetic radiation intensity or a plurality of such detectors which monitor the change occurring in a number of fringes or the entire interference pattern. The one or more detectors may comprise one or more photodetectors (eg photodiodes). Where more than one photodetector is used this may be arranged in an array.

A plurality of electromagnetic radiation detector units (eg in an array) and/or a plurality of electromagnetic radiation sources may be used to measure in discrete areas of the sensor component simultaneously the responses to changes in the localised environment. Alternatively, the position of the electromagnetic radiation detector and electromagnetic radiation source relative to the sensor component may be changed to provide information concerning responses in discrete areas of the sensor component. For example, discrete responses to a change in the localised environment caused by the presence of the same or different stimuli may be measured in discrete areas of the sensor component. In the first instance, concentration gradients of the same stimulus may be deduced. In the second instance, discrete responses to changes in the localised environment may be measured in different regions. For this purpose, the preferred assembly makes use of the versatility of the evanescent mode and comprises a plurality of separate sensing layers or regions.

The sensor component may be excited across its width and a two-dimensional photodiode array (or the like) may be used to effectively interrogate "strips" of the sensor component (eg an array sensor). This may be carried out across more than one axis simultaneously or sequentially to provide spatially resolved information relating to events on the surface of the sensor component.

Conveniently, electrodes positioned in contact with a surface of the sensing layer or sensing waveguide enable capacitance to be measured simultaneously. The electrodes may take the form of either parallel plates laid alongside a plurality of planar waveguides or as an interdigitated or meander system laid down on the top and bottom surfaces of the sensing waveguide or sensing layer or adjacent to it. In the case of a meander system, the metal forming the electrode is responsible for absorbing excessive amounts of light and as such the capacitance is measured on an adjacent structure which is not utilised for optical measurement.

In an embodiment of the sensor assembly of the invention, analyte containing a chemical or biological stimulus may be continuously introduced into the localised environment eg in a discontinuous flow. Alternatively changes in a static chemical stimulus may be caused by inducing a change (such as any of those described hereinbefore) in the analyte containing a chemical or biological stimulus which is static in the localised environment (and in this sense the system is dynamic).

Preferably the sensor assembly of the invention comprises means for intimately exposing at least a part of the (or each) sensing layer or the sensing waveguide of the sensor component to the localised environment. The sensor component may permit precise measurements to be made either across the entire architecture or at discrete areas thereby enabling effective integration with the means for intimately exposing at least a part of the sensing layer or the sensing waveguide to the localised environment. Thus in a preferred embodiment, the means for intimately exposing at least a part of the sensing layer or the sensing waveguide to the localised environment is integrated onto the sensor component.

Preferably the means for intimately exposing at least a part of the sensing layer or the sensing waveguide to the localised environment is adapted to permit the continuous introduction of an analyte containing a chemical stimulus of interest (ie a dynamic system). For example, it may permit the continuous introduction of the stimulus of interest in a discontinuous flow (eg as a train of discrete portions) into the localised environment. This may be achieved by capillary action or by a separate urging means.

Preferably the means for intimately exposing at least a part of the sensing layer or the sensing waveguide to the localised environment is adapted to induce chemical reactions in a static analyte containing a chemical stimulus of interest. In this sense, the system may be considered to be dynamic. Chemical reactions may be induced in any conventional manner such as by heat or radiation.

The means for intimately exposing at least a part of the (or each) sensing layer or the sensing waveguide to the localised environment may be a part of a microstructure positionable on the surface of and in intimate contact with the sensor component.

Preferably the microstructure comprises means for intimately exposing at least a part of the sensing layer or the sensing waveguide to the localised environment in the form of one or more microchannels and/or microchambers. For example, an analyte containing chemical stimuli may be fed through microchannels or chemical reactions may take place in an analyte located in a microchamber. An analyte containing chemical stimuli may be fed into the microchannels by capillary action or positively fed by an urging means.

In a preferred embodiment, the means for intimately exposing at least a part of the (or each) sensing layer or the sensing waveguide to the localised environment is included in a cladding layer. For example, microchannels and/or microchambers may be etched into the cladding layer. The cladding layer may perform optical functions such as preventing significant discontinuities at the boundary of the sensing waveguide or sensing layer(s) or chemical functions such as restricting access of certain species to the sensing waveguide or sensing layer(s). The cladding layer may be integrated onto the sensor component.

Preferably, the whole of or a portion of any additional functionality may be included in the cladding layer. In one embodiment, the sensing layer itself may be incorporated in the cladding layer (for example in the form of an absorbent material). Particularly preferably, the whole of the additional functionality may be provided in the cladding layer and include sensing devices such as for example quadrature electric field tracks or other microfluidic sensing devices. The cladding layer may incorporate an electromagnetic source (eg a laser) and/or means for detecting electromagnetic radiation (of the type detailed below). The cladding layer may incorporate a chemical separating means (eg an HPLC based device).

Viewed from an even further aspect the present invention provides a kit of parts comprising: a sensor assembly as hereinbefore defined, a first electromagnetic radiation source capable of providing TM mode excitation, a second electromagnetic radiation source capable of providing TE mode excitation and one or more detectors in an array.

The first and second electromagnetic radiation source may be the same or different. Preferably the kit comprises a controller adapted to synchronise the one or more electromagnetic radiation sources and one or more detectors.

Viewed from a yet still further aspect the present invention provides the use of a sensor assembly according to the first aspect of the invention for measuring changes in dimension (eg thickness) and/or composition (ie intrinsic refractive index) of a sensor component caused by the presence of or changes in a chemical or physical stimulus (eg a chemical, physical or biological stimulus) in a localised environment.

Preferably the use of the sensor assembly is for measuring specific and/or non-specific binding (eg a biosensor).

Preferably the use of the sensor assembly is for measuring conformational change of the stimulus (eg a protein).

Preferably the use of the sensor assembly is for identifying effective nucleotide complementation.

Preferably the use of the sensor assembly is for detecting ingress into or depletion from a sensing layer or sensing waveguide.

Preferably the use of the sensor assembly is for detecting expansion or contraction of the sensing layer or sensing waveguide (eg in the form of a thin film).

Preferably the use of the sensor assembly is as a biosensor eg for determining the characteristics of adsorption of large non-spherical biological molecules from aqueous solution (the film thickness would be indicative of the orientation and the refractive index indicative of the density of adsorption).

The term "optical" used herein means radiation of any wavelength in the electromagnetic spectrum capable of generating polarisations in a medium.

It will be obvious to those having skill in the art that many changes may be made to the details of the above-described embodiments of this invention without departing from the underlying principles thereof. The scope of the present invention should, therefore, be determined only by the following claims.

Figure 1:
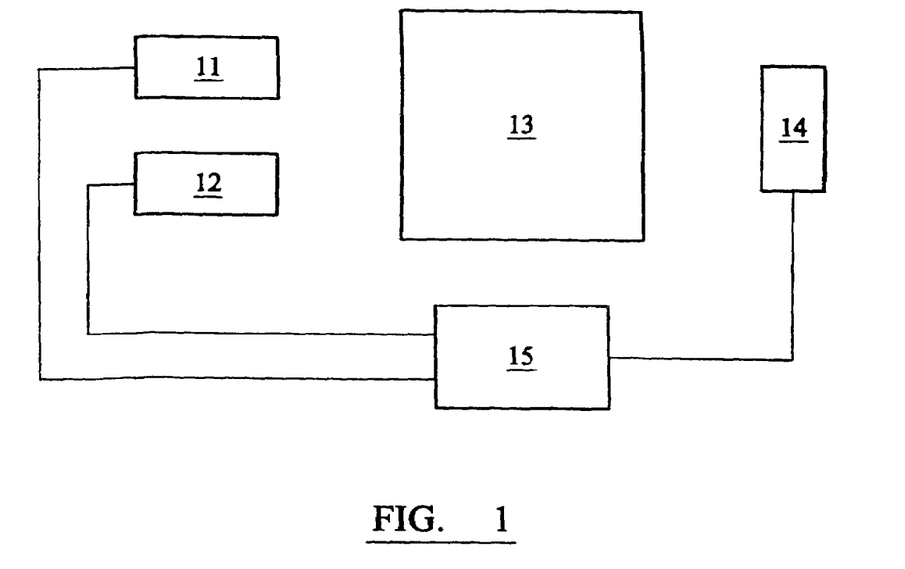
FIG. 1 represents an embodiment of the invention schematically in plan view.

An embodiment of the method of the invention is shown schematically in FIG. 1. Plane polarised electromagnetic radiation is generated in TM mode using a first electromagnetic radiation source (11) and in TE mode using a second electromagnetic radiation source (12) relative to the sensor component (13). The sensor component is of a multi-layered type as described hereinafter by way of example with reference to FIG. 4 or of the type described in a PCT application filed in the name of Farfield Sensors Limited claiming priority from GB9927249.4 with the title Sensor Device.

An interference pattern is captured by the photodiode or photodiode array (14). The two electromagnetic radiation sources (11 and 12) are controlled electronically by a controller (15) that also captures the data from the photodiode array (14). The firing of each of the electromagnetic radiation sources (11) and (12) is synchronised by the controller (15) such that the interference patterns in TM mode and TE mode are alternately captured. The controller (15) calculates the phase shift in each mode and the two phase shifts are compared in order to calculate the factors contributing to the changes in effective refractive index (as described hereinafter). This data may be reported directly or made available to secondary systems for further analysis.

Figure 2:
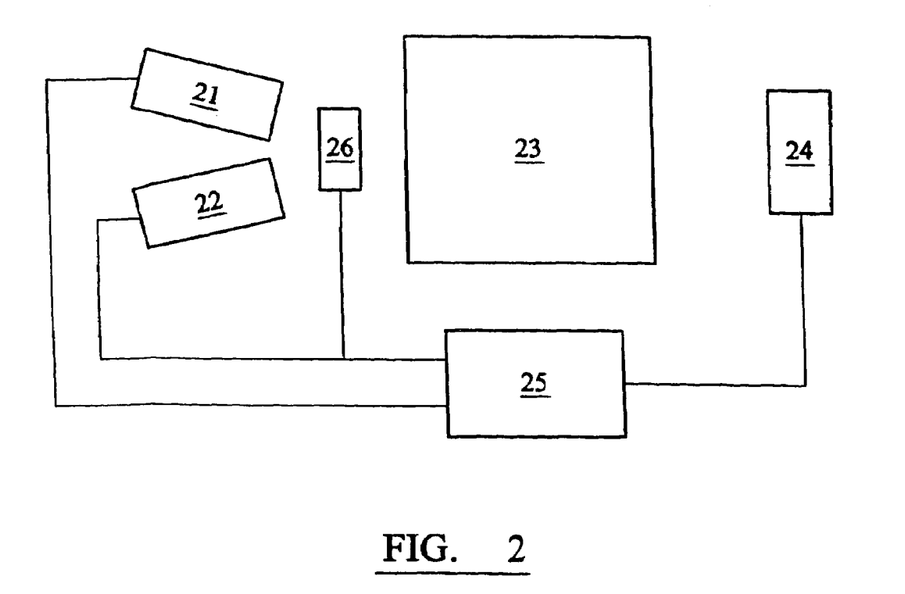
FIG. 2 represents an embodiment of the invention schematically in plan view.

A further embodiment is shown schematically in FIG. 2 in which a rotating mirror (26) is employed to switch rapidly between electromagnetic radiation in TE and TM mode from first and second electromagnetic radiation sources (21) and (22) respectively for irradiating sensor component (23). A controller (25) is arranged to synchronise the electromagnetic radiation sources (21) and (22), the optical switch (26) and the photodiode array (24).

Figure 3:
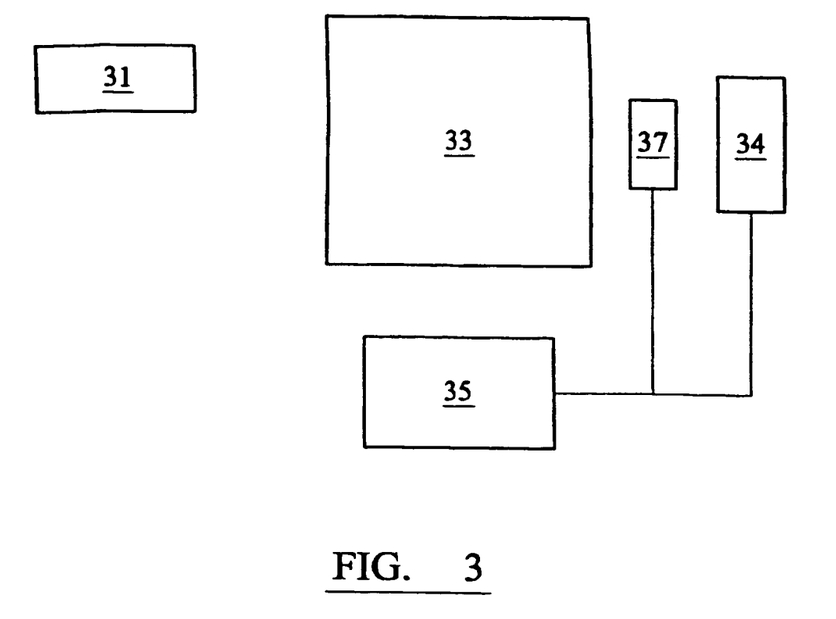
FIG. 3 represents an embodiment of the invention schematically in plan view.

In FIG. 3, a single electromagnetic radiation source (31) is used to simultaneously irradiate the sensor component (33) with electromagnetic radiation in TE and TM modes. This is achieved by aligning the polarisation vector of the linearly polarised optical source at an angle of 45< with respect to the plane of the sensing layer or sensing waveguide of the sensor component (33). An active analyser system (37) is used to remove unwanted output of TE or TM radiation during capture of the output of desired TM or TE radiation respectively. This may consist of an electro-optic half wave plate placed in series with an analyser. A controller (35) is arranged to synchronise the source (31), the analyser system (37) and the photodiode array (34).

EXAMPLE 1

This Example describes the use of two discrete polarisation modes in accordance with the method of the invention to differentiate the contributions to changes in the effective refractive index of changes in dimension (eg thickness) and composition (ie intrinsic refractive index) of a sensing layer.

In general, continuous measurements of the phase accumulation of a sensor assembly may be made using TE and TM polarisation. This may be achieved by alternating the input between TE and TM polarisation or by alternately analysing the output of the TE and TM polarisation respectively (as described hereinbefore). The difference in the accumulated phase after a change in the localised environment (caused by layer deposition for example) is available as data for inputting into a suitable algorithm designed to yield the contributions (to the change in effective refractive index) of changes in dimension (eg thickness) and composition (ie intrinsic refractive index) as a unique related pair of data.

This may for example be achieved using standard waveguide modelling packages where starting with the known initial waveguide structure, subsequent layers can be fitted in the model by varying the parameters in an iterative manner. The effect of thin film formation on a sensor component as defined in Table 1 and shown schematically in FIG. 4 has been modelled. By way of example, the formation of a certain thickness of film (5) which causes a phase shift of 273 radians in TE polarisation mode may correspond to several combinations of the contribution to changes in the effective refractive index of changes in thickness and intrinsic refractive index. Two such possible combinations are a film of thickness 5.2 nm with an intrinsic refractive index of 1.5 or a film of 7 nm thickness with an intrinsic refractive index of 1.4. If the phase shift is measured in TM mode, these combinations may be distinguished as the former combination would produce a phase change of 536 radians and the latter a change of 577 radians. The measured phase change in TM mode thus defines the unique contribution of thickness and intrinsic refractive index from the possibilities deduced from measurement in TE mode. The result yields an average film thickness and intrinsic refractive index by assuming a homogeneous layer. This technique is analogous with techniques of wavelength modulation described in for example Williams et al, J Appl phys., 60, (1986), 1900.

TABLE 1

Figure 4:
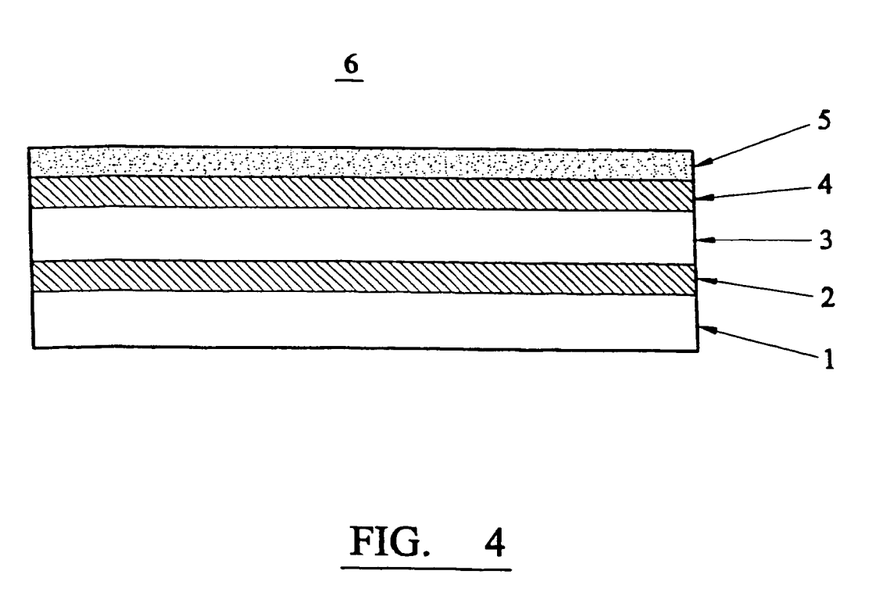
FIG. 4 represents a sensor component upon which has been formed a thin film.

| Layer | Thickness/μm | Refractive Index |
|---|---|---|
| 1 | 1 | 1.49 |
| 2 | 0.2 | 1.95 |
| 3 | 1 | 1.47 |
| 4 | 0.2 | 2.0005 |
| 5 | Variable | variable |
| 6 | Infinite | 1 (air) |

More complex structures may be resolved with the aid of a suitable model.

The derivative use of these measurements would be to determine the orientation of adsorption of large non-spherical biological molecules from aqueous solution. The film thickness would be indicative of the orientation and the refractive index indicative of the density of adsorption.

EXAMPLE 2

In accordance with the method of the invention, a change in the thickness and intrinsic refractive index of a sorbent layer resulting from absorbtion of a vapour or liquid analyte may be measured. If the initial intrinsic refractive index and thickness of the layer is known, then the final thickness and intrinsic refractive index may also be determined in a similar manner to example 2. Knowing the change in thickness and intrinsic refractive index of the film enables the effective refractive index per unit volume of the analyte to be calculated. The effective refractive index will be a function of the intrinsic refractive index of the analyte and the packing density within the polymeric sorbent layer. This is likely to be characteristic of the analyte being adsorbed and may be used as a means of identification. Where the packing of the analyte into the layer is ideal, the effective refractive index of the analyte will equal its intrinsic refractive index.

What is claimed is:

1. A sensor assembly for measuring one or more factors contributing to a change in the effective refractive index of a sensor component thereof caused by the introduction of or changes in a stimulus in a localised environment, wherein said sensor component includes either:
   (1) one or more sensing layers capable of inducing a measurable response to a change in the localised environment caused by the introduction of or changes in the stimulus; or
   (2) a sensing waveguide capable of exhibiting a measurable response to a change in the localised environment caused by the introduction of or changes in the stimulus,
   said sensor assembly further comprising:
       first irradiating means for irradiating the sensor component with electromagnetic radiation in TM mode;
       second irradiating means for irradiating the sensor component with electromagnetic radiation in TE mode;
       a measuring means for measuring the measurable response; and
       a synchronising means for synchronising the measuring means with the first and second irradiating means so as to correlate the measurement of the measurable response with the irradiation of the sensor component with electromagnetic radiation in TE and TM modes.

2. The assembly according to claim 1 wherein the measurable response is a movement in an interference pattern.

3. The assembly according to claim 1 wherein the first and second irradiating means are adapted to irradiate the sensor component with electromagnetic radiation in TE or TM mode sequentially or simultaneously.

4. The assembly according to claim 1 wherein the first and second irradiating means comprise the same or different electromagnetic radiation sources.

5. The assembly according to claim 4 wherein the first and second irradiating means comprise different electromagnetic radiation sources, said assembly further comprising an optical switch for switching rapidly between the two sources.

6. The assembly according to claim 5 wherein the optical switch is a rotating mirror.

7. The assembly according to claim 4 wherein the first and second irradiating means comprise the same electromagnetic radiation source capable of irradiating the sensor component simultaneously with TE and TM modes by aligning the polarisation vector at an angle of 45< with respect to the plane of the sensing waveguide or sensing layer.

8. The assembly according to claim 7 further comprising an active analyser system for alternately removing unwanted output radiation in TE or TM mode during capture of the desired output radiation in TM or TE mode respectively.

9. The assembly according to claim 8 wherein the active analyser system includes an electro-optic half wave plate placed in series with an analyser.

10. The assembly according to claim 1 wherein the synchronising means is capable of calculating the phase shift of the output radiation in TE and TM mode independently.

11. The assembly according to claim 1 wherein the synchronising means is capable of relating the movements in the first and second interference patterns to changes in dimension and/or composition of the sensing waveguide or sensing layer.

12. The assembly according to claim 1 wherein the synchronising means is capable of relating the movements in the first and second interference patterns to ingress of a chemical stimulus into or depletion of a chemical stimulus from the sensing layer or the sensing waveguide.

13. The assembly according to claim 1 wherein the synchronising means is capable of relating the movements in the first and second interference patterns to the expansion or contraction of the sensing layer or sensing waveguide.

14. The assembly according to claim 1 wherein the synchronising means is capable of relating the movements in the first and second interference patterns to the characteristics of adsorption of large non-spherical biological molecules from an aqueous solution.

15. The assembly according to claim 14 wherein the characteristics of adsorption are molecular orientation and/or density of adsorption.

16. The assembly according to claim 1 wherein the synchronising means is capable of relating the movements in the first and second interference patterns to specific and/or non-specific binding.

17. The assembly according to claim 16 wherein the specific and/or non-specific binding is of an antibody/antigen specific binding pair.

18. The assembly according to claim 1 wherein the synchronising means is capable of relating the movements in the first and second interference patterns to a conformational change of the stimulus.

19. The assembly according to claim 18 wherein the stimulus is a protein.

20. The assembly according to claim 1 wherein the synchronising means is capable of relating the movements in the first and second interference patterns to an effective nucleotide complementation.

21. The assembly according to claim 1 wherein the sensor component includes one or more sensing layers capable of inducing in a secondary waveguide a measurable response to a change in the localised environment caused by the introduction of or changes in the stimulus.

22. The assembly according to claim 1 wherein the sensor component includes a sensing waveguide capable of exhibiting a measurable response to a change in the localised environment caused by the introduction of or changes in the stimulus.

23. The assembly according to claim 1 wherein each of the sensing waveguide or secondary waveguide of the sensor component is a planar waveguide.

24. The assembly according to claim 1 wherein the sensor component constitutes a multi-layered structure.

25. An assembly as claimed in claim 1 wherein in the synchronising means comprises:
    a controller adapted to synchronise the filing of the first and second irradiating means with the alternate capture of the interference patterns generated in TE and TM mode.

26. A method for measuring one or more factors contributing to a change in the effective refractive index of a sensor component caused by the introduction of or changes in a stimulus in a localised environment, said method comprising:
    (A) providing a sensor assembly as defined in claim 1;
    (B) introducing the stimulus into the localised environment;
    (C) irradiating the sensor component with electromagnetic radiation in TE mode to produce a first interference pattern;
    (D) irradiating the sensor component with electromagnetic radiation in TM mode to produce a second interference pattern;
    (E) measuring movements in the first interference pattern;
    (F) measuring movements in the second interference pattern; and
    (G) relating the movements in the first and second interference patterns to the one or more factors contributing to a change in the effective refractive index of the sensor component.

27. The method according to claim 26 wherein the one or more factors are changes in dimension and/or composition of either the one or more sensing layers or the sensing waveguide.

28. The method according to claim 26 wherein the one or more factors are specific and/or non-specific binding.

29. The method according to claim 28 wherein the specific and/or non-specific binding is of an antibody/antigen specific binding pair.

30. The method according to claim 26 wherein the one or more factors are a conformational change of the stimulus.

31. The method according to claim 30 wherein the stimulus is a protein.

32. The method according to claim 26 wherein the one or more factors are an effective nucleotide complementation.

33. The method according to claim 26 wherein the one or more factors are ingress of a chemical stimulus into or depletion of a chemical stimulus from the sensing layer or the sensing waveguide.

34. The method according to claim 26 wherein the one or more factors are expansion or contraction of the sensing layer or sensing waveguide.

35. The method according to claim 26 wherein the one or more factors are the characteristics of adsorption of large non-spherical biological molecules from an aqueous solution.

36. The method according to claim 35 wherein the characteristics of adsorption are the film thickness and/or the density of adsorption.

37. The method according to claim 26 further comprising: calculating the phase shift from the movements in the first and second interference patterns.

38. A sensor assembly for measuring one or more factors contributing to a change in the effective refractive index of a sensor component thereof caused by the introduction of or changes in a stimulus in a localised environment, wherein said sensor component includes either:
    (1) one or more sensing layers capable of inducing a measurable response to a change in the localised environment caused by the introduction of or changes in the stimulus; or
    (2) a sensing waveguide capable of exhibiting a measurable response to a change in the localised environment caused by the introduction of or changes in the stimulus,
    said sensor assembly further comprising:
    first irradiating means for irradiating the sensor component with electromagnetic radiation in TM mode; and
    second irradiating means for irradiating the sensor component with electromagnetic radiation in TE mode, and
    wherein the first and second irradiating means comprise the same electromagnetic radiation source capable of irradiating the sensor component simultaneously with TE and TM modes by aligning the polarisation vector at an angle of about 45° with respect to the plane of the sensing waveguide or sensing layer.

39. An assembly as claimed in claim 38 wherein the measurable response is a movement in an interference pattern.

40. An assembly as claimed in claim 38 further comprising an active analyser system for alternately removing unwanted output radiation in TE or TM mode during capture of the desired output radiation in TM or TE mode respectively.

41. An assembly as claimed in claim 40 wherein the active analyser system includes an electro-optic half wave plate placed in series with an analyser.

* * * * *